United States Patent [19]
McClure

[11] 3,945,374
[45] Mar. 23, 1976

[54] BIOMEDICAL SIGNAL PROCESSING

[76] Inventor: Robert Bruce McClure, 3325 Stumphall Road, Collegeville, Pa. 19426

[22] Filed: Jan. 25, 1974

[21] Appl. No.: 436,507

[52] U.S. Cl. ............................. 128/2.1 M; 330/69
[51] Int. Cl.² ........................................ A61B 5/04
[58] Field of Search...... 128/2.06 A, 2.06 B, 2.06 F, 128/2.06 G, 2.1 B, 2.1 M, 2.1 R, 2.1 Z; 330/29, 69, 144, 145; 328/115, 169, 172, 235 R, 235 A

[56] References Cited
UNITED STATES PATENTS

| | | | |
|---|---|---|---|
| 2,673,559 | 3/1954 | Fawcett........................... | 128/2.06 B |
| 2,902,030 | 9/1959 | Kennedy et al. ................ | 128/2.1 M |
| 3,451,006 | 6/1969 | Grongaard, Jr. ............... | 128/2.06 B |
| 3,569,852 | 3/1971 | Berkovits ....................... | 128/2.06 B |
| 3,656,474 | 4/1972 | Gentry et al. .................. | 128/2.1 M |

*Primary Examiner*—William E. Kamm
*Attorney, Agent, or Firm*—Charles A. McClure

[57] ABSTRACT

A biomedical signal processor and process for converting a composite physiologically generated signal having both electrocardiographic and electromyographic components into an electromyographic signal free of interference from electrocardiographic signals. Suppression of the electrocardiographic component is accomplished by conversion of overall gain to zero whenever the signal amplitude exceeds a predetermined setting corresponding to maximum electromyographic signal.

8 Claims, 5 Drawing Figures

BIOMEDICAL SIGNAL PROCESSING

This application relates to processing of electronic signals having a physiological origin, especially so as to eliminate interference from unwanted signals.

In preparation of an electromyogram, as in recording action of the diaphragm located between the chest and abdominal cavities, other signals of physiological origin, such as from the heart, may interfere. Whereas electromyographic signals are longer in duration, electrocardiographic signals usually have greater peak amplitude. Prior attempts to filter the latter from the former proved unsatisfactory.

A primary object of the present invention is elimination of electrocardiographic signal interference in preparation of electromyograms.

Another object is selection of an electromyographic signal from a composite signal having an electrocardiographic component. A further object is design of reliable apparatus for accomplishing the foregoing objects effectively and economically.

Yet another object of this invention is utilization of integrated circuit components in the design of the foregoing apparatus and for performing the foregoing process steps.

Other objects of the present invention, together with means and methods for attaining the various objects, will be apparent from the following description of a preferred embodiment and accompanying diagrams, presented by way of example rather than limitation.

In general, the objects of the present invention are accomplished, in conjunction with biomedical electrographic apparatus, by electronic circuitry for suppressing electrocardiographic, rather than electromyographic, signals. This is achieved, in processing a composite signal having electrocardiographic and electromyographic components, for use in preparation of an electromyogram, by establishing a predetermined signal level normally exceeded by the electrocardiographic component signal but not by the electromyographic component signal and suppressing any signal exceeding such predetermined signal level.

More particularly, the invention provides electronic circuit means for eliminating electrocardiographic signal interference with electromyographic signals, comprising means for receiving both electrocardiographic and electromyographic signals together, means for producing reference signals bounding the normal maximum electromyographic signal, and means for suppressing any signals outside the bounds of such reference signals.

Figures 1, 4:
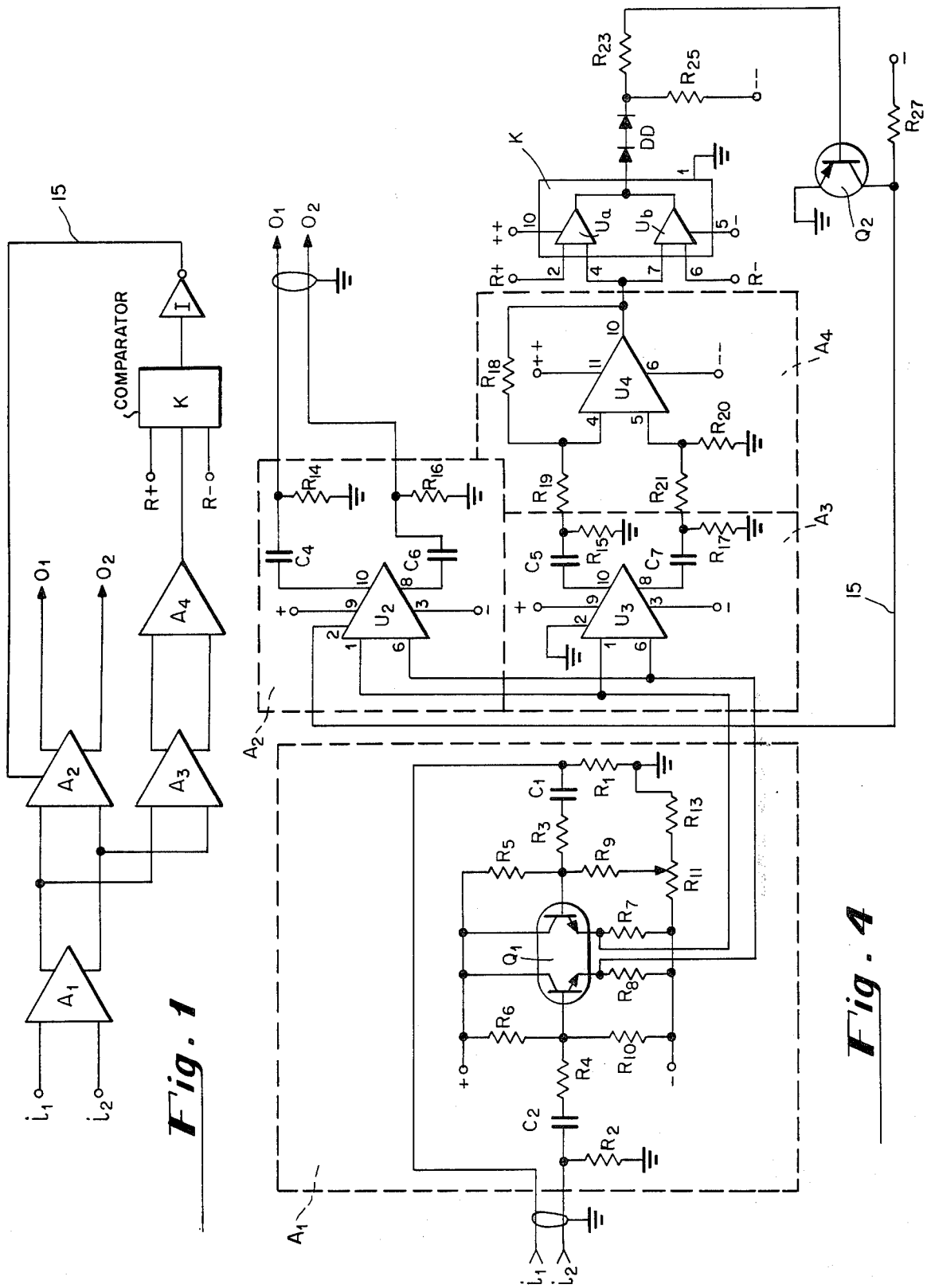
FIG. 1 is a schematic view of principal apparatus components of the present invention.
FIG. 4 is a circuit diagram corresponding to the schematic diagram of FIG. 1.

FIG. 1 shows, in block form, principal components of apparatus of this invention, including amplifiers $A_1$ to $A_4$, inclusive. Differential amplifiers $A_2$ and $A_3$ are connected in parallel to receive the outputs of differential amplifier $A_1$, which receives the signal input at terminals $i_1$, $i_2$. The outputs of differential amplifier $A_2$ from terminals $O_1$, $O_2$ go to suitable electrographic apparatus (not shown). The outputs from differential amplifier $A_3$ form the input for amplifier $A_4$, whose single-ended output is fed into dual comparator K along with reference signals R+ and R− provided by the auxiliary circuitry shown in the next view. The single-ended output from the comparator is fed to inverter I, from which the output is fed back via lead 15 to differential amplifier $A_2$ for the purpose of gain control.

Figure 2:
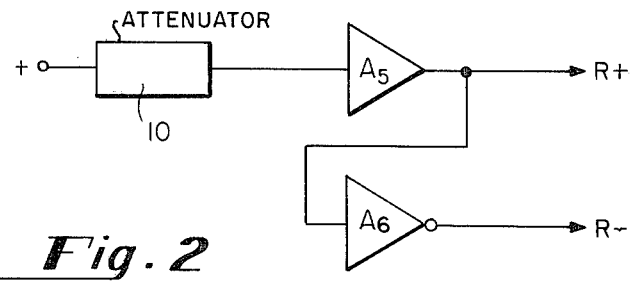
FIG. 2 is a similar view of auxiliary apparatus components of this invention.

FIG. 2 shows, also in block form, auxiliary apparatus for preparing and presetting the amplitude of the reference signals. Variable attenuator 10 supplied with unvarying positive signal + at its input is connected at its output to the input of amplifier $A_5$, which produces reference signal R+. The same output (R+) is applied to the input of inverter $A_6$, which produces reference signal R−. Appropriate d.c. power supply means to provide unvarying single and double amplitude positive signals (+, ++) and corresponding negative signals (−, −−) may be wholly conventional and is omitted from the drawings in the interest of simplicity, not being necessary to an understanding of the invention.

Figure 3:
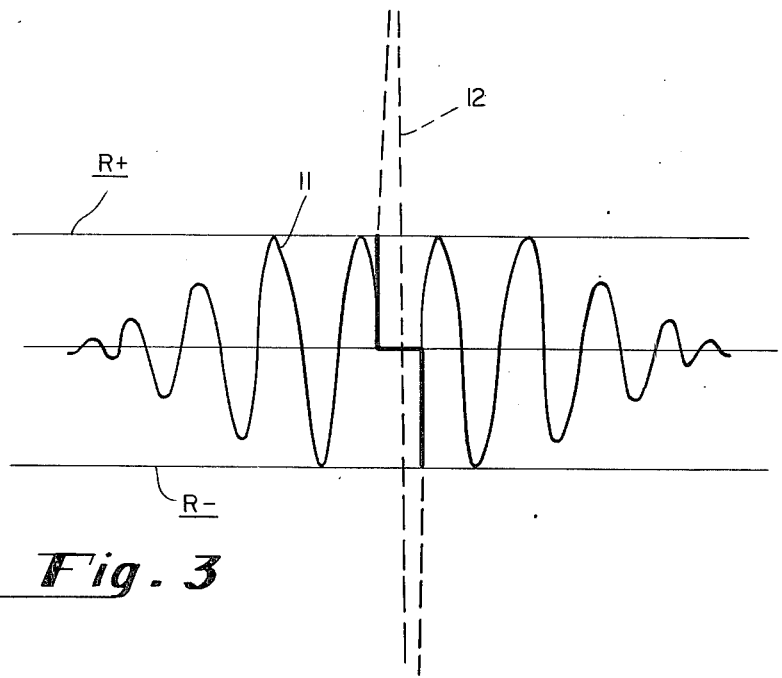
FIG. 3 is a graphical representation of signals processed by such apparatus.

FIG. 3 shows in graphical form, rather stylized for simplicity, the effects of this invention on a composite signal having an electromyographic signal component 11 of relatively long duration and low amplitude and an electrocardiographic signal component 12 of relatively short duration and high amplitude. The maximum amplitude of the electromyographic signal is bounded by positive reference signal amplitude R+ and by negative reference signal amplitude R−. The portions of the electrocardiographic signal outside the reference amplitude limits is shown in broken lines because it is suppressed according to this invention, and the output signal during such excessive input signal is zero. Except for such suppression the output signal is a direct amplification of the input signal.

FIG. 4 shows circuitry corresponding to the block diagram of FIG. 1. Differential amplifier $A_1$ (outlined in broken lines) is made up of dual transistor $Q_1$, and associated circuit elements. Input from terminal $i_1$, which has resistor $R_1$ to ground, is a.c.-coupled to the base electrode of the right half of $Q_1$, via capacitor $C_1$ and resistor $R_3$, while input from terminal $i_2$, separated from ground by resistor $R_2$, is a.c.-coupled similarly to the left base of $Q_1$ via capacitor $C_2$ and resistor $R_4$. Both collector electrodes of $Q_1$ are tied directly to positive potential +, and the respective base leads have resistors $R_5$ and $R_6$ thereto. The emitter electrode leads go to negative potential − through respective resistors $R_7$ and $R_8$. The left-hand base electrode has resistor $R_{10}$ between it and negative potential −, while the right-hand base electrode has corresponding resistor $R_9$ to a voltage divider made up of adjustable part $R_{11}$ and fixed part $R_{13}$ connected between − and ground.

Differential amplifiers $A_2$ and $A_3$ of FIG. 1 are represented (outlined in broken lines) in FIG. 4 as integrated circuits $U_2$ and $U_3$ plus associated leads and circuit elements. Both emitters of transistor $Q_1$ are connected as inputs to both $U_2$ and $U_3$, which are identical, at terminals 1 and 6 of each. Terminals 9 of each are supplied with positive potential +, and terminals 3 of each with negative potential −. Leads from terminals 10 and 8 of integrated circuit $U_2$ go to respective output terminals $o_1$, $o_2$ through respective coupling capacitors $C_5$ and $C_6$ having resistors $R_{14}$ and $R_{16}$ to ground at the output side.

Similar output leads from integrated circuit $U_2$ are coupled to respective input terminals 4 and 5 of integrated circuit $U_4$ of single-ended output amplifier $A_4$ (outlined in broken lines). The first such lead contains capacitor $C_5$, series resistor $R_{19}$, and resistor $R_{15}$ to ground from their common junction; the second lead contains capacitor $C_7$, series resistor $R_{21}$, and ground resistor $R_{17}$. Terminals 11 and 6 of $U_4$ are connected to positive potential ++ and negative potential —, respectively. Single output terminal 10 is connected to input terminal 4 (inverting) through resistor $R_{18}$, while input terminal 5 has resistor $R_{20}$ to ground.

Figure 5:
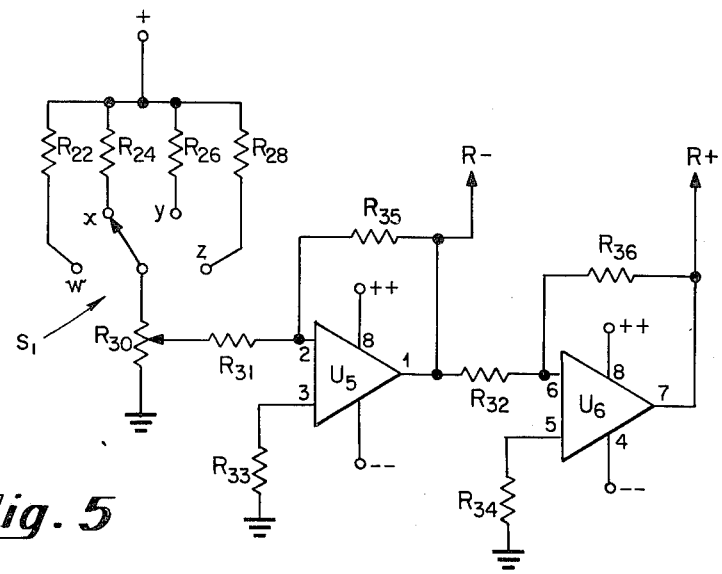
FIG. 5 is a similar diagram corresponding to the auxiliary showing in FIG. 2.

Comparator K comprises pair of like integrated circuits $U_a$ and $U_b$, each of which has an input terminal (4 and 7, respectively) connected to the output terminal of $U_4$, while the other input terminals (2 and 6) connect to adjustable reference potentials R+ and R—, respectively (see FIGS. 2 and 5). The comparator is supplied with positive potential ++ at terminal 10 and with negative potential — at terminal 5, and terminal 1 is grounded. Output terminal 9 common to both $U_a$ and $U_b$ is d.c.-coupled to the base electrode of transistor $-Q_2$ of inverter I (shown in FIG. 1, not separately outlined here) through double diode DD and series resistor $R_{23}$, with resistor $R_{25}$ from their common junction to negative potential —. The emitter electrode of $Q_1$ is grounded and the collector electrode, which has resistor $R_{27}$ to negative potential —, is tied by feedback lead 15 to terminal 2 of integrated circuit $U_2$ of differential amplifier $A_2$. FIG. 5 shows auxiliary circuitry corresponding to the block diagram of FIG. 2, and it will be understood without the necessity of outlining the several blocks in this view that the left-hand part comprises variable attenuator 10, the central part amplifier $A_5$ and the right-hand part amplifier $A_6$. The attenuator includes resistors $R_{22}$, $R_{24}$, $R_{26}$, and $R_{28}$, each with one end tied to positive potential + and with their opposite ends terminating at switch terminals $w$, $x$, $y$, and $z$, respectively. Switch arm $S_1$ (shown engaging terminal $x$) connects to adjustable resistor $R_{30}$, the other end of which connects to ground, and the slider of which connects through resistor $R_{31}$ to the amplifier portion of the circuitry. $U_5$ and $U_6$ are integrated circuit halves with associated circuit elements of amplifier $A_5$ and $A_6$. Resistor $R_{31}$ connects to inverting input terminal 2 of $U_5$, whose other input terminal has resistor $R_{33}$ to ground. Terminals 8 and 4, respectively, are tied to positive potential ++ and negative potential —. Output terminal 1 of $U_5$ is connected to input terminal 2 thereof through resistor $R_{35}$ and to inverting input terminal 6 of $U_2$ via resistor $R_{32}$. Its other input terminal has resistor $R_{34}$ to ground; terminals 8 and 4 are tied to positive potential ++ and negative potential —; and output terminal 7 is connected to output terminal 6 through resistor $R_{36}$. The respective output terminals of $U_5$ and $U_6$ provide reference potentials R— and R+ (see FIGS. 2 and 5).

Operation of this apparatus is readily understood. The positive and negative reference potentials are adjusted by setting switch arm $S_1$ to one of contacts $w$, $x$, $y$, and $z$, and adjustable resistor $R_{30}$ is set so that R+ and R— are of such amplitude (but opposite sign, of course) to bound the maximum expected electromyographic signal level at the comparator Any signal in excess of such level has the effect of precluding any output to the related electrographic apparatus (not shown).

In detail, an electric signal input at terminals $6_1$, $i_2$ (as from a physiological source) is treated by differential amplifier $A_1$, the respective halves of transistor $Q_1$ acting upon opposite halves of the signal, to provide a suitable impedance match and an overall amplification of about 0.1 (i.e., a tenfold attenuation). Differential amplifiers $A_2$ and $A_3$ provide a maximum gain of many times more than that (e.g., 30) to give a positive overall gain (such as 3). Their inputs and outputs are both a.c.-coupled, resulting in zero d.c. output component. Amplifier $A_4$, which is stabilized at a gain of one by feedback through $R_{18}$, converts the differential output of $A_3$ to a single-ended signal for comparison with reference signal levels in dual comparator K. When the positive swing of the signal exceeds R+ or its negative swing exceeds R— the output (from the corresponding integrated circuit component) goes positive and—after inversion by invertor I—is fed back through gain control line 15 to amplifier $A_2$, which it cuts off (i.e., reduces to essentially zero amplification).

If the reference potentials bound the maximum electroymographic signal fairly closely, the net effect will be to pass essentially all the electromyographic signal (amplified several times). Whenever an electrocardiographic signal is received, its peak amplitude normally exceeds the reference potentials and, at and beyond such bounds, precludes any signal output. The brevity of such electrocardiographic signal produces only a slight interruption in signal duration upon co-occurrence with an electromyographic signal and may be ignored or damped out in the electrographic apparatus. In the absence of an electromyographic signal sich an electrocardiographic signal would be damped out likewise or give rise to only a momentary spike within the reference potential limits.

If the electromyographic signal at its normal maximum amplitude exceeds the reference potential limits (or is exceeded thereby) the variable attenuator is readily adjusted to narrow or eliminate the difference as may be desired. Accordingly, this invention has effectively eliminated electrocardiographic interference from electromyographic signal recording. It has done so conveniently, economically, and reliably.

For further guidance to those interested in practicing this invention the following table presents suitable identification or values of circuit components or elements.

| | | | | | | | | |
|---|---|---|---|---|---|---|---|---|
| $C_1$ | 0.3μf | $R_1$ | 10M | $R_{11}$ | 5K | $R_{22}$ | 5K | $R_{33}$ | 51K |
| $C_2$ | 0.3μf | $R_2$ | 10M | $R_{13}$ | 20K | $R_{23}$ | 9.1K | $R_{34}$ | 5.1K |
| $C_4$ | 2.2μf | $R_3$ | 1M | $R_{14}$ | 51K | $R_{24}$ | 25K | $R_{35}$ | 100K |
| $C_5$ | 2.2μf | $R_4$ | 1M | $R_{15}$ | 1M | $R_{25}$ | 5.1K | $R_{36}$ | 10K |
| $C_6$ | 2.2μf | $R_5$ | 205K | $R_{16}$ | 51K | $R_{26}$ | 95K | $U_a$ | ½711 |
| $C_7$ | 2.2μf | $R_6$ | 205K | $R_{17}$ | 1M | $R_{27}$ | 3.9K | $U_b$ | ½711 |
| DD | 1N714 | $R_7$ | 27K | $R_{18}$ | 100K | $R_{28}$ | 295K | $U_2$ | CA3000 |
| K | 711 | $R_8$ | 27K | $R_{19}$ | 100K | $R_{30}$ | 5K | $U_3$ | CA3000 |
| $Q_1$ | QD102 | $R_9$ | 240K | $R_{20}$ | 100K | $R_{31}$ | 100K | $U_4$ | 741 |
| $Q_2$ | 2N4126 | $R_{10}$ | 240K | $R_{21}$ | 1M | $R_{32}$ | 10K | $U_5$ | ½MC1458 |

| | U₆ | ½MC1458 |
|---|---|---|

Although a preferred embodiment of the invention has been shown and described, modifications may be made therein, as by adding, combining, or subdividing parts or steps or by substituting equivalents while retaining advantages and benefits of the invention, which itself is defined in the following claims.

I claim:

1. For use in conjunction with biomedical electrographic apparatus including means delivering output therefrom to a recorder actuatable thereby, electronic circuit means for eliminating electrocardiographic signal interference with electromyographic signals, comprising means for receiving both electrocardiographic and electromyographic signals, including an input differential amplifier, two parallel differential amplifiers each connected to receive the outputs of the input differential amplifier; means for producing reference signals bounding the normal maximum electromyographic signal, including a reference signal generator having means for generating positive and negative reference signals, a dual comparator connected to receive and compare the outputs of one of the parallel amplifiers and the respective reference signals; and means operatively connected to both the foregoing means for suppressing any signals outside the bounds of such reference signals preparatory to actuating the recorder thereby, including gain control means connected to receive the output of the comparator and effective to reduce the gain of the other parallel amplifier, which is the output amplifier for suitable recording means, and including means for connecting the output of the latter amplifier to such recording means.

2. Electronic circuit means according to claim 1, wherein the means for signal suppression includes means responsive to the signal level for attenuating all signals outside the bounds of the reference signals.

3. Electronic circuit means according to claim 2, wherein the amplifier means is effective to amplify signals not attenuated thereby.

4. Electronic circuit means comprising an input differential amplifier for receiving and acting upon composite electromyographic and electrocardiographic signals of relatively long duration and relatively great peak signal level, respectively, two parallel differential amplifiers each connected to receive the outputs of the input differential amplifier, a reference signal generator including means for generating positive and negative reference signals, a dual comparator connected to receive and compare the respective outputs of one of the latter amplifiers and the respective reference signals, and gain control means connected to receive the output of the comparator and effective to reduce the gain of the other parallel amplifier, which is the output amplifier for suitable recording means, whenever the reference signal level is exceeded, and including means for interconnecting the output of the latter amplifier to such recording means.

5. Electronic circuit means according to claim 4, including a dual to single-ended signal converter including means for converting a differential signal into a single-ended signal connected between the first parallel differential amplifier and the comparator.

6. Electronic circuit means according to claim 4, including voltage divider means operatively connected to the comparator for adjusting the reference signal level.

7. Electronic circuit means according to claim 4, including an inverter connected between the output of the comparator and gain control means of the output differential amplifier.

8. Electronic circuit means according to claim 4, wherein the input differential amplifier has a gain of about one-tenth and the parallel differential amplifiers have a gain of about 30, the first of the latter amplifiers being operable at full gain when the reference signal level is not exceeded and at zero gain when the reference signal level is exceeded.

* * * * *